United States Patent [19]

Danziger et al.

[11] 4,157,986
[45] Jun. 12, 1979

[54] ABRASION RESISTANT CATALYST

[75] Inventors: Harry Danziger; Otto Immel; Bernd-Ulrich Kaiser; Hans-Helmut Schwarz; Eberhard Bandtel, all of Krefeld, Fed. Rep. of Germany

[73] Assignee: Bayer Aktiengesellschaft, Leverkusen, Fed. Rep. of Germany

[21] Appl. No.: 832,012

[22] Filed: Sep. 9, 1977

[30] Foreign Application Priority Data

Sep. 15, 1976 [DE] Fed. Rep. of Germany ....... 2641389

[51] Int. Cl.² .................... B01J 21/02; C07D 210/00
[52] U.S. Cl. ............................. 252/432; 260/239.3 R
[58] Field of Search ........................................ 252/432

[56] References Cited

U.S. PATENT DOCUMENTS

| | | | |
|---|---|---|---|
| 3,154,539 | 10/1964 | Irnich | 252/432 X |
| 3,294,860 | 12/1966 | Loft et al. | 252/432 X |
| 3,574,193 | 4/1971 | Immel et al. | 252/432 X |
| 3,833,560 | 9/1974 | Immel et al. | 252/432 X |
| 4,028,273 | 6/1977 | O'Hara et al. | 252/432 |

FOREIGN PATENT DOCUMENTS

| | | | |
|---|---|---|---|
| 1802887 | 7/1970 | Fed. Rep. of Germany | 252/432 |
| 1670816 | 4/1971 | Fed. Rep. of Germany | 252/432 |
| 394092 | 1974 | U.S.S.R. | 252/432 |

*Primary Examiner*—Delbert E. Gantz
*Assistant Examiner*—William G. Wright
*Attorney, Agent, or Firm*—Connolly and Hutz

[57] ABSTRACT

A process for the preparation of catalyst granulates from carbon black, boric acid, water and optionally nitrogenous additives, characterized in that from 3 to 50% by weight of a finely divided catalyst, which has already been used for the preparation of caprolactam and which has optionally been regenerated, are added.

3 Claims, No Drawings

ABRASION RESISTANT CATALYST

Abrasion resistant catalysts of boric acid and carbon black for the gas phase molecular rearrangement of cyclohexanone oxime to caprolactam in a fluidised bed reactor are already known (see German Offenlegungsschrift No. 1,670,816). These catalysts are usually used in the form of granulates. The granulates may be prepared by the method of synthetic granulation of finely divided carbon black, finely divided boric acid, water and optionally nitrogenous additives. The method of synthetic granulation has been described in the Journal "Aufbereitungstechnik" No. 11,1971.

The granules of catalysts used for molecular rearrangement of cyclohexanone oxime are generally required to have a particular size and particle size distribution. Such granulates are very difficult to prepare and accurate reproduction of the size, form, and size distribution of the granulates is practically impossible.

The present invention provides a process for the preparation of catalyst granulates from carbon black, boric acid, water and optionally nitrogenous additives, wherein from 3 to 50% by wt. based on the weight of the total mixture of a finely divided catalyst, which has already been used for the preparation of caprolactam and which has optionally been regenerated, is added.

The addition of this catalyst results in an astonishing improvement in the reproducibility of the required particle size and size distribution and furthermore in an improvement in the abrasion resistance of the catalyst and the distribution of boric acid in it.

The catalysts which have already been used for the preparation of caprolactam are preferably those which are normally removed for regeneration, after a certain operating time, from the reactors used in the gas phase conversion of cyclohexanone oxime to caprolactam. Instead of returning these used catalysts to the process after they have been regenerated, they are ground down to particle sizes of, generally, less than 0.1 mm and used in accordance with the invention.

In the gas phase rearrangement of cyclohexanone oxime to caprolactam in a fluidised bed, part of the catalyst is generally lost from the particles by abrasion and discharged as dust from the reactor, together with the reaction gases. This dust is separated off and in most cases discarded. It has now been found that this catalyst dust is particularly suitable for the process of the invention.

EXAMPLE 18 parts by weight of boric acid, 12 parts by weight of carbon black from exhaust gas, 0.75 parts by weight of urea and 8.25 parts by weight of size-reduced catalyst, which has already been used for cyclohexanone oxime conversion to caprolactam by the process according to German Pat. No. 1,802,887 and which has been recovered therefrom by air regeneration via a cyclone separator, are intensively mixed in a mixing screw manufactured by the Nauta company. The mixture is then milled in a Bauermeister mill and sprayed with 16 parts by weight of water in a second Nauta mixer. The moistened mixture is then formed into pellets by spraying it with water on a granulating plate. The pellets are then dried in a circulating air-drying cupboard, first for eight hours at room temperature and then for eight hours at 300° C. The dried pellets are annealed for three hours at 580° C. in a rotary furnace through which a slow stream of nitrogen is passed. The resulting catalyst pellets are sieved. The yield of pellets having diameters from 0.4 to 1.2 mm, which is the range suitable for the molecular rearrangement, amounts to 72% by weight of the total pellets.

(a) To determine the amount of abrasion, 50 g of catalyst were introduced into a glass tube 5 cm in width which had a glass frit base through which a stream of nitrogen was introduced to keep the catalyst in vigorous motion for 200 hours. At the end of this time, the fine dust formed by abrasion was removed by sieving the catalyst through a sieve with a 0.4 mm mesh and the residue was weighed. The abrasion, measured by the difference between the final weight and the initial weight, was less than 0.01 g.

(b) 120 g of cyclohexanone oxime and 360 liters of nitrogen were passed over 10 g of the catalyst of the 0.4–1.2 mm fraction for 6 hours at 340°–350° C. and 760 Torr. The cyclohexanone oxime contained 4% by weight of water. The condensed reaction product corresponded to a conversion of 98% by weight of a yield of 98% by weight of caprolactam based on the quantity of cyclohexanone oxime reacted.

What we claim is:

1. A process for the preparation of a catalyst granulate, which comprises mixing carbon black, boric acid, water and from 3 to 50% by weight, based on the total weight, of a finely divided boric acid-carbon black catalyst which has previously been used for the preparation of caprolactam from cyclohexanone oxime and forming a granulate from the resulting mixture.

2. A process as claimed in claim 1, wherein the finely divided catalyst has a particle size of 0.1 mm or less.

3. A process as claimed in claim 1, wherein urea is also included in the mixture.

* * * * *